United States Patent [19]
Cocuzza et al.

[11] Patent Number: 5,484,701
[45] Date of Patent: Jan. 16, 1996

[54] METHOD FOR SEQUENCING DNA USING BIOTIN-STREPAVIDIN CONJUGATES TO FACILITATE THE PURIFICATION OF PRIMER EXTENSION PRODUCTS

[75] Inventors: Anthony J. Cocuzza; Frank W. Hobbs, Jr.; Robert J. Zagursky, all of Wilmington, Del.; Neil A. Straus, North York, Canada

[73] Assignee: E. I. Du Pont de Nemours and Company, Wilmington, Del.

[21] Appl. No.: 829,857

[22] Filed: Jan. 31, 1992

Related U.S. Application Data

[63] Continuation of Ser. No. 471,144, Jan. 26, 1990, abandoned.
[51] Int. Cl.$^6$ .............................. C12Q 1/68; C12P 19/34
[52] U.S. Cl. ........................ 435/6; 435/91.2; 435/91.5; 435/91.53; 935/77; 935/78
[58] Field of Search .............................. 435/6, 91, 91.1, 435/91.5, 91.53, 91.2; 436/63, 94, 501, 508, 518; 935/76, 77, 78; 937/77, 78

[56] References Cited

U.S. PATENT DOCUMENTS 4,908,453   3/1990   Cocuzza .................................. 548/113

FOREIGN PATENT DOCUMENTS

| | | |
|---|---|---|
| 0097373 | 10/1984 | European Pat. Off. . |
| 0192168 | 8/1986 | European Pat. Off. .................... 435/6 |
| 8703911 | 7/1987 | WIPO . |
| 8707645 | 12/1987 | WIPO ...................................... 435/91 |
| 8810313 | 12/1988 | WIPO . |
| 8909282 | 10/1989 | WIPO . |
| 8912063 | 12/1989 | WIPO . |

OTHER PUBLICATIONS

W. W. Barnes, *Methods in Enzymology*, vol. 152, pp. 538–555 (1987).
H. Delius, et al., *Nucleic Acids Research*, vol. 13, No. 15, pp. 5457–5469 (1985).
R. W. Richardson, et al. *Nucleic Acids Research*, vol. 11, No. 18, pp. 6167–6184.
A. Chollet, et al., *Nucleic Acids Research*, vol. 13, No. 5, pp. 1529–1541.
T. Manning, et al., *Biochemistry*, vol. 16, No. 7, pp. 1364–1370.
Wittig et al. (Biochem. Biophys. Res. Comm., 91, 554–562, 1979).
Wilchek et al., Anal. Biochem., 171, 1–32, 1988.
Mitchell et al., Anal. Biochem., 178, 239–242, 1989.
Eckermann et al., European J. of Biochem., 82, 225–234, 1978.
Shimkus et al., Proc. Natl. Acad. Sci. USA, 82, 2593–2597, 1985.
Landegren et al., Science, 241, 1077–1080, 1988.
Richtenick, Nucleic Acids Res., 17, 2181–2186, 1989.
Hultman et al., Nucleic Acids Res., 17, 4937–4946, 1989.
Green, Advances in Protein Chemistry, 29, 85–133, 1975.
Sanger et al., Proc. Natl. Acad. Sci. USA, 74, 5463–6467, 1977.
Prober et al., Science, 238, 336–341, 1987.
Saiki et al., Science, 230, 1350–1355, 1985.
Cocuzza, Tetrahedron Letters, 30, 6387–6290, 1989.
Ogden et al., Methods in Enzymology, in Berger (Ed.), Guide to Molecular Techniques, 152, 63, 1987.
Zagursky et al., Gene Anal., Techn. 2:89–94 (1985).
Kroeker et al., Biochem., vol. 15(20) 4463 (1976).
Bio Techniques, vol. 4, No. 4 (1986) "Effects of Detergents on Avidin–Biotin Interaction" 350–354.
Ross et al., BioTechniques 4(4):350–354 (Jul./Aug. 1986).
Hong, "Sequencing of Large Double–Stranded DNA Using the Dideoxy Sequencing Technique", Bioscience Reports 2:907–912 (1982).
Wilchek et al Anal Biochem 171, 1–32, 1988.
Richardson et al, Nucleic Acids Res, 11, 6167–84, 1983.
Green et al., The Dissociation of Avidin–Biotin Complexes by Guanidium Chloride, Biochem. J., 130, 707–711, 1972.

*Primary Examiner*—Stephanie W. Zitomer

[57] ABSTRACT

A simplified method for isolating primer extension products and generating them in a form appropriate for electrophoresis is disclosed. The method is compatible with automated DNA sequencing procedures.

29 Claims, 7 Drawing Sheets

METHOD FOR SEQUENCING DNA USING BIOTIN-STREPAVIDIN CONJUGATES TO FACILITATE THE PURIFICATION OF PRIMER EXTENSION PRODUCTS

This is a continuation of application Ser. No. 07/471,144, filed Jan. 26, 1990, now abandoned.

FIELD OF THE INVENTION

This invention relates to a simplified method for isolating primer extension products and generating them in a form appropriate for gel electrophoresis.

BACKGROUND OF THE INVENTION

The Sanger chain-termination sequencing method and the Polymerase Chain Reaction (PCR) are two powerful methods for analyzing DNA which are certain to become even more widely used in the near future. These procedures both use the template-directed extension of an oligonucleotide primer by a DNA polymerase followed by the analysis of the primer extension products, most often by gel electrophoresis. The analysis of these extension products is often complicated by the presence of the other reaction components which comprise the bulk of the mixture and which are difficult and tedious to remove. Thus, both methods would benefit from a simplified procedure for the isolation of these primer extension products from other reaction components and for the generation of them in a form appropriate for gel electrophoresis. In addition to Sanger sequencing and PCR, other primer extension reactions are being developed which will benefit from such a procedure.

The worldwide effort to sequence the human genome will require many thousands of Sanger sequencing reactions. By using fluorescence detection, the GENESIS 2000™ (E. I. du Pont de Nemours and Co., Wilmington, Del.) greatly simplifies and automates the electrophoretic analysis of Sanger sequencing reactions. However, the work-up of these reactions requires the use of spin columns or precipitations to remove unincorporated fluorescent terminators followed by the evaporation of a large volume of eluting solvent. Since processing a large number of sequencing reactions is very tedious, a faster, simplified work-up procedure is highly desirable. Standard radioisotope-based Sanger sequencing reactions of plasmid DNA normally do not require any work-up prior to gel electrophoresis. However, sequencing reactions of more complex DNA such as cosmid, lambda clone, or genomic DNA generate primer extension products contaminated with large amounts of template DNA and/or extraneous labeled DNA fragments which tend to interfere with gel electrophoresis. Sequencing of complex DNA would benefit from a simple procedure for isolation of the labeled extension products from the other reaction components.

The Polymerase Chain Reaction (PCR) is likely to become integral to the new field of DNA diagnostics. The technique generates two amplified complementary strands of DNA in the presence of double-stranded template. By means of multiple primer extension reactions, millions of double stranded copies of a specific region of a template that lies between two primers are produced. Analysis of the amplified DNA (for example by sequencing or direct gel electrophoresis) is best performed on a single strand of DNA uncontaminated with the complementary strand or the template. Analysis would be facilitated by the availability of a simple procedure for the isolation of the extension products from the other reaction components.

The biotin-avidin (streptavidin) system is a very useful analytical tool and is utilized in a wide variety of bioanalytical applications. The proteins avidin and streptavidin (hereinafter referred to jointly as "strept/avidin") form exceptionally tight complexes with biotin ($K_D = 10^{-15}$M) and certain analogs of biotin. In general, when biotin is coupled to a second large or small molecule through its carboxyl side chain, the resulting conjugate is still tightly bound by strept/avidin. The second molecule is said to be "biotinylated" when such conjugates are prepared. The biotin-strept/avidin binding pair is utilized in a wide variety of bioanalytical applications. These applications generally involve complexation of a biotinylated analyte to strept/avidin followed by detection, analysis, or use of the complex. For a review of this field, see Wilchek et al. (Anal. Biochem., 171, 1–32, 1988). In a few cases, the complex between the biotinylated analyte and strept/avidin is disassociated before the analysis is complete. The simple complex between biotin and avidin can be disassociated by: heating at 132° C. (but it reforms on cooling) or denaturation with 6M guanidine hydrochloride at low pH. Due to the harshness of these conditions, complexation of a biotinylated analyte can be considered to be effectively an irreversible process. Such dissociation conditions are likely to destroy many biological analytes.

The biotin-strept/avidin complex has been used frequently in the analysis of biotinylated nucleic acids. However, there are only three reports concerning the disassociation of such complexes.

Disclosures involving biotinylated nucleic acids include the misinterpretation by Mitchell et al., (Anal. Biochem., 178, 1–4, 1989) of Delius et at. (Nucleic Acids Res., 13, 5457–5469, 1988) that biotinylated single-stranded DNA fragments could be dissociated from avidin-agarose by 50% guanidine isothiocynate/formamide at room temperature. In fact, Delius et al., disclose a method that separates complementary strands of biotinylated DNA, but does not dissociate the biotinavidin complex from the DNA strands with formamide. Other disclosures include the report by Richardson et al. (Nucleic Acids Res., 11, 6167–6184, 1983) that a biotinylated ribonucleotide trimer could be eluted from an avidin-agarose column with a large quantity of 6M guanidine hydrochloride (pH 2.5); the report by Eckermann et al. (European J. of Biochem., 82, 225–234, 1978) that the complex between avidin and biotinylated ribosomal RNA could be disrupted by treatment with 70% formic acid for 10 minutes at room temperature.

In the above three disclosures, the biotinylated nucleic acids released from strept/avidin were not carefully analyzed to prove that the released nucleic acid was unmodified and that all of the binding protein had been removed from the biotin subunit. In fact, Delius asserts that the biotinylated nucleic acid eluted from a solid-supported avidin was still complexed to some of the binding protein. Treatment of nucleic acids with acid in general, and formic acid in particular, is known to cause depurination and eventually strand cleavage. Therefore complex dissociation under the above conditions might be expected to release modified nucleic acid for analysis. The most common and sensitive method for analyzing nucleic acids is gel electrophoresis, but there are serious obstacles to analyzing nucleic acids decomplexed as described above. Both 6M guanidine hydrochloride (pH 2.5) and 70% formic acid are likely to be incompatable with gel electrophoresis. Fifty percent guanidine isothiocyanate in formamide is also a less than optimum choice since samples with high salt content tend to produce poorly resolved electrophoresis bands. The use of any of these three methods to dissociate biotinylated sequencing fragments from solid supported avidin or streptavidin would likely require further treatment of the resulting solution of fragments before analysis by polyacrylamide gel electrophoresis. In conclusion, successful electrophoretic analysis of biotinylated nucleic acids disassociated from strept/avidin is problematical and has not been previously demonstrated.

A related disclosure by Shimkus et al. (Proc. Natl. Acad. Sci. USA, 82, 2593–2597, 1985) reports that DNA probes containing biotin attached through a chemically cleavable disulfide group bind to avidin-agarose columns and can be eluted from the column with aqueous dithiothreitol which breaks the disulfide bond, leaving the biotin-avidin complex on the column. The use of disulfide linkages is not preferred because many enzymes require the presence of thiols for activity. There are three techniques known in which 5'-biotinylated oligonucleotides are used as primers in template directed extension reactions; however, in none of these is the biotin-avidin complex broken nor can the biotinylated extension products be analyzed by gel electrophoresis. In one disclosure, Mitchell et al. (Anal. Biochem., 178, 1–4, 1989) describe a method for direct dideoxy sequencing following PCR in which the biotinylated extension product is captured by solid-supported streptavidin and the complementary strand is removed by base denaturation; however, the biotin-streptavidin bond is never broken, and it is the unbiotinylated complementary strand which is analyzed by dideoxy sequencing. In another disclosure, Landegren et al (Science, 241, 1077–1081, 1988) describe a method for ligase-mediated gene detection in which a 5'-biotinylated primer is ligated to a radioactively-labeled oligonucleotide in a template directed manner and the now labeled biotinylated strand is captured by solid-supported streptavidin beads; the beads are then analyzed for the presence of a label, again without breaking the biotin-streptavidin bond. In a third disclosure, Richterich (Nucleic Acids Res., 17, 2181–2186, 1989) describes a method for non-radioactive sequencing of DNA in which a 5'-biotinylated primer is used in a Sanger sequencing reaction, not to isolate the sequencing fragments but only to detect them.

Hultman et al (Nucleic Acids Res., 17, 4937–4946, 1989) disclose a method for direct solid phase sequencing of genomic and plasmid DNA using ferromagnetic beads as a support. In this sequencing procedure the template (not the fragments) is biotinylated and attached to streptavidin Dynabeads™ (Dynal, Inc.). Again, the resulting biotin-streptavidin bond is never broken.

SUMMARY OF THE INVENTION

The purpose of the present invention is to provide a process which greatly simplifies the isolation of primer extension products freed from other materials (ie. enzymes, DNA, buffer salts) and generates them in a form appropriate for gel electrophoresis, based on both the ability of the biotin-avidin(streptavidin) system to form a very tight binding complex and an improved method of disassociating that complex when desired. Furthermore, this method lends itself to automation of DNA sequencing and PCR.

In brief, the invention includes the following steps which are described in greater detail in the following section:

a. extending a biotinylated primer by means of a template-directed primer extension reaction;

b. complexing the biotinylated primer extension products of step a to a biotin-binding protein supported on a solid, said complexing performed either before or after separating the template from the biotinylated primer extension products of step a;

c. separating physically the complexed biotinylated primer extension products of step b from the liquid phase of the primer extension reaction;

d. treating the complex of step c with a denaturant to dissociate the biotinylated primer extension products from the biotin-binding protein supported on a solid; and e. Analyzing the primer extension products by electrophoresis.

Other aspects of this invention include variations in the order in which primer extension, complexation, and strand separation steps are performed.

DETAILED DESCRIPTION OF THE INVENTION

Applicants' invention provides a simplified method for isolating primer extension products from template-directed DNA polymerase reactions.

For the purposes of this application, the following terms and phrases are important to an understanding of the invention:

"Primer" means a single stranded oligonucleotide capable of hybridizing at one or more specific locations or "priming sites" in the template nucleic acid. "Primer extension product" means a primer to which one or more naturally occurring or modified nucleotides have been added by template directed enzymatic addition to the 3' end of the primer. The process requires hybridization of the primer to the template. "Biotinylated primer" means a primer covalently linked to a biotin or an analog of biotin. The linking group used should permit enzymatic primer extension and hybridization between the primer and the template. The binding of biotin and analogs of biotin to avidin is reviewed by Green (Advances in Protein Chemistry, 29, 85–133, 1975).

"Template" means a single or double stranded nucleic acid to be analyzed by means of primer extension reactions. "Template-directed polymerase reaction" or "primer extension reaction" includes, but is not limited to, a standard Sanger sequencing reaction (Sanger et al., Proc. Natl. Acad. Sci. U.S.A., 74, 5463–5467, 1977), a fluorescent terminator sequencing reaction (Prober et al., Science, 238, 336–341, 1987), PCR (Saiki et al., Science, 230, 1350–1355, 1985), or some other template-directed primer extension reaction such as ligase-mediated gene detection (Landegren et al., Science, 241, 1077–1081, 1988).

Figure 1:
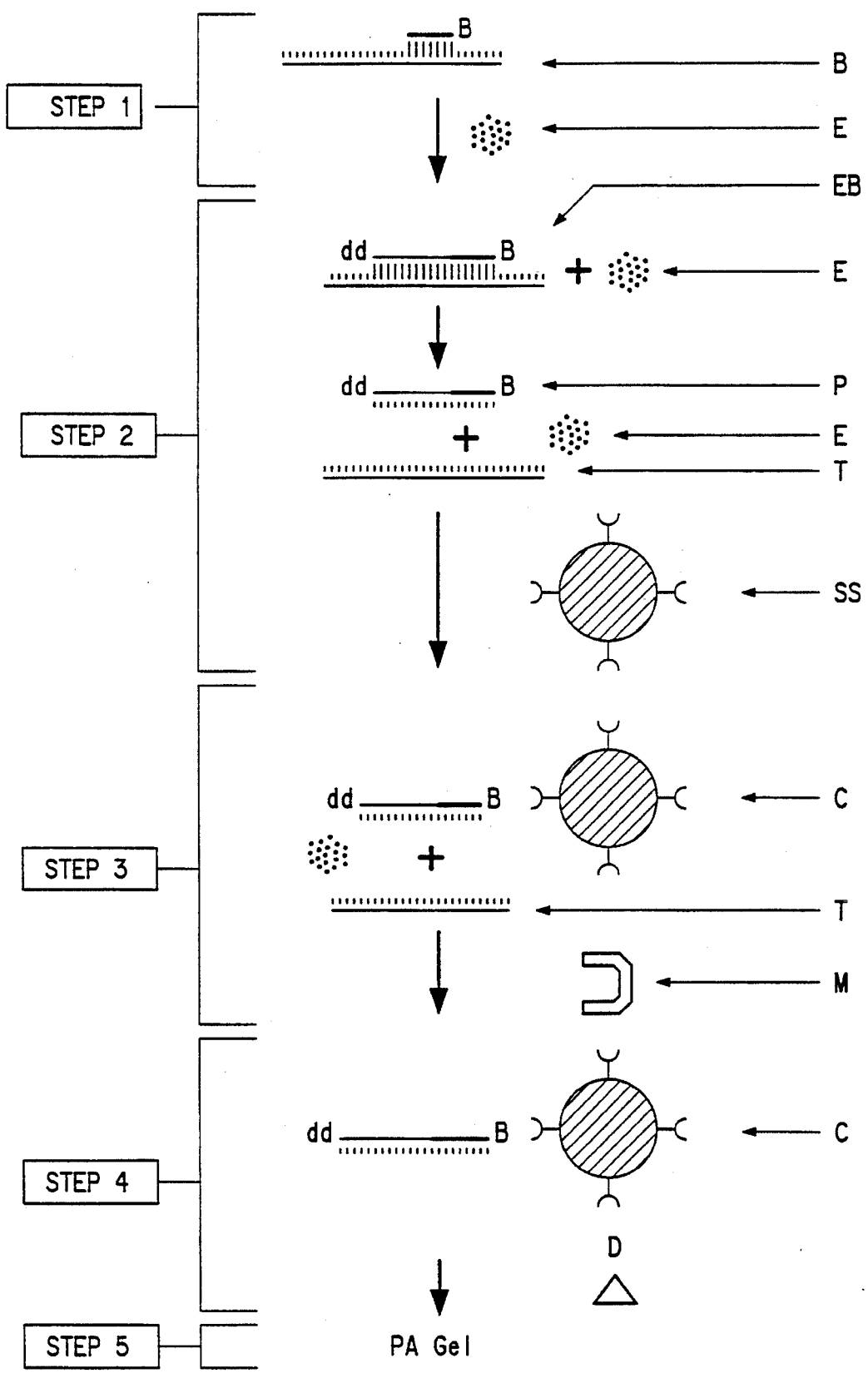
FIG. 1 is a schematic drawing of the purification of biotinylated primer extension products where said products are captured by a solid supported streptavidin on ferromagnetic beads in the presence of excess template.
Figure 2:
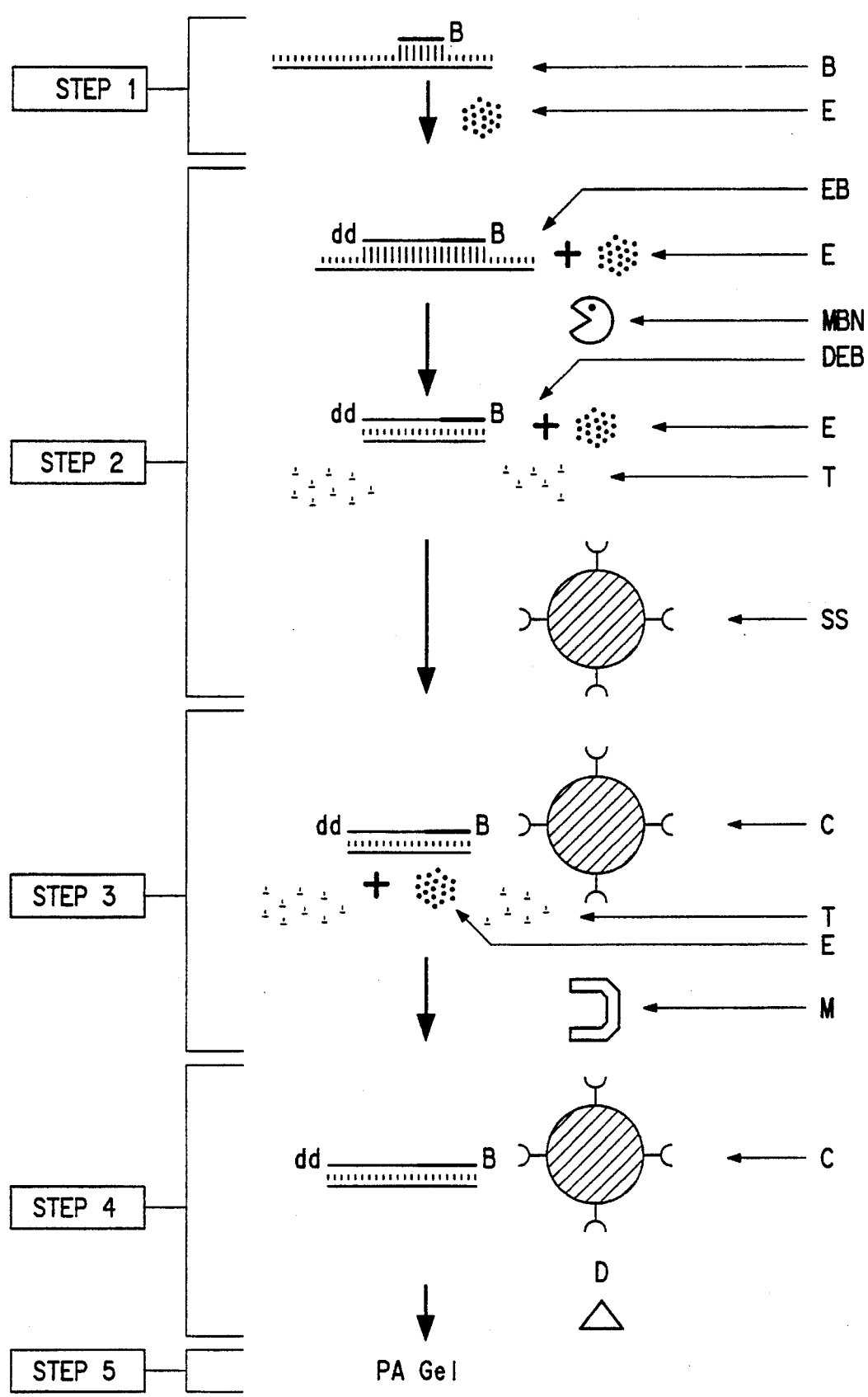
FIG. 2 is a schematic drawing of the purification of biotinylated primer extension products where said products are captured by a solid supported streptavidin on ferromagnetic beads where excess template has been digested by an enzyme such as mung bean nuclease.

FIG. 1 illustrates one embodiment of Applicants' invention and FIG. 2 illustrates a second embodiment. The only difference between these two processes occurs in step 2, wherein a different method is used to separate template from biotinylated primer extension products. In fact, as shown in the figures and described more fully below, these operational differences result in differences in the structure of the captured nucleic acids. In the first step of both embodiments, a biotinylated primer (B) is required, and it is preferred that the biotin be attached to the 5'-nucleotide of the primer, most preferably through the 5'-hydroxyl group. Several methods are described in the art for the preparation of 5'-biotinylated oligonucleotide primers (B), but the most useful is described by Cocuzza (Tetrahedron Letters, 30, 6287– 6290, 1989). In FIGS. 1 and 2, "E" represents the enzyme, a polymerase, which effects primer extension by attaching conventional, modified, or tagged deoxy- and/or dideoxy-nucleotide substrates to the primer. Appropriate conditions for effecting such primer extension reactions are well known in the art. The desired products of step 1 (EB) are double-stranded nucleic acids consisting of a template strand and a (biotinylated) primer extension product strand. These products are contaminated with a large excess of nucleotide substrates, enzyme, buffer salts, and non-biotinylated nucleic acids arising from impurities in the template. As discussed above and demonstrated in the examples section, DNA sequence analysis is improved by the process described below for removing these contaminants before electrophoretic analysis. (Most or all of the template strand (T) is also removed.) DNA amplification by PCR affords products containing the same contaminants. The product of step 1 is an extended biotinylated primer (EB).

In the second step of this invention, a complex (C) is formed between the biotinylated primer extension products (P) and solid-supported strept/avidin (SS). This may be carried out directly on the crude material, but it is preferable to first separate all or most of the template DNA (T) from the extension products, since the template DNA (T) which is annealed to the primer extension products (P) tends to interfere with this process. Methods of denaturing DNA are well known in the art. One method of doing this is to heat denature the DNA duplexes by warming the extension reaction mixture at a temperature between 25° C. and 100° C., with warming at 95° C. being most preferred. Alternatively, one may denature the DNA duplexes by chemical means, for example: treatment with strong base, with treatment with sodium hydroxide being most preferred; with treatment with formaldehyde or urea (Ogden et al., Methods in Enzymology, in Berger (Ed.), Guide to Molecular Techniques, 152, 63, 1987), treatment with 5–60% formamide at a temperature between 40° C. and 80° C., with treatment with 30% formamide at 70° C. being most preferred.

The above methods for complexation fit the details shown in FIG. 1. An alternative method for complexation is shown in FIG. 2. In this method, most of the template DNA (T) is destroyed prior to complexation by treatment of the products of step 1 with a single strand nuclease, preferably with a nuclease which cleaves only single stranded DNA. Mung bean nuclease (MBN) is most preferred. This nuclease procedure digests the single stranded region of the template DNA leaving each primer extension product annealed to a short piece of complementary DNA. In FIG. 2, this unit of material is a digested extended biotinylated primer (DEB). Of these alternative methods for separating all or most of the template DNA from the extension products, the heat treatment denaturing method is most preferred to assist complex formation in step 2.

Complexation of the biotinylated primer extension products is accomplished by adding a biotin-binding protein immobilized on a solid support. This solid-supported biotin-binding protein may be, for example, avidin, streptavidin, or an anti-biotin antibody, but is preferably streptavidin. A variety of solid supports can be used including: polymeric beads, such as agarose or sepharose; paper, glass or plastic surfaces; and metal particles (hereafter called magnetic particles) capable of being physically separated from reaction mixtures with the aid of a magnet. Commerically available examples of solid-supported biotin-binding proteins include: avidin-agarose (Bethesda Research Laboratories), streptavidin-coated chromium dioxide particles (E. I. dupont de Nemours and Co., Wilmington, Del.), or streptavidin-coated Dynabeads™ (Dynal, Inc.). Dynabeads™ are the most preferred solid-supported biotin-binding protein. The complexation reaction is not particularly sensitive to reaction conditions and is most conveniently carried out under the existing reaction conditions with occasional agitation. The complexation reaction may be carried out from 0° to 100°, but most preferably at room temperature at pH 3–9.

In the third step of this invention, the solid phase, which consists of solid-supported strept/avidin complexed to biotinylated primer extension products (C), is separated from the liquid phase which contains the bulk of the other components of the primer extension reaction. These components include the polymerase, the template, the reaction buffer, and any unincorporated nucleoside. When streptavidin-coated ferro-magnetic beads (SS) are used, the separation step is done by holding a magnet (M) next to the reaction vessel to capture the magnetic beads, which permits the drawing off of the liquid phase. It is preferred that the beads (SS) be washed to remove lingering contaminants.

The advantages of separating out the components listed above include:

1. eliminating the need to use spin columns or precipitations to remove the reaction components;

2. removing the bulk of reaction components which could otherwise interfere with the resolution of the invention's analysis step;

3. preventing rehybridization of the template to the primer;

4. removing side products generated by non-biotinylated primers that may be present; and 5. removing the bulk of the solvents to permit release of the primer extension in a more concentrated form for later use. Furthermore, the separation of the liquid phase from the solid phase is condusive to the automation of the invention.

In the fourth step of this invention, the complex (C) between the biotinylated primer extension products (P) and the solid-supported avidin or streptavidin is dissociated and biotinylated primer extension products are separated from the solid supported avidin or streptavidin. This is done by treating the solid material with a denaturant (D) capable of breaking the protein-biotin complex. The denaturant mixture is preferably compatible with electrophoresis which is the next step in the method. It is preferred to use formamide from 20° C. to 120° C. with 90° C. to 100° C. most preferred. Denaturants which did not work were 7M urea, 6M guanidine-HCl and 70% formic acid. Fifty percent guanidine isothiocyanate/formamide produced electrophesis bands unsatisfactorily resolved as compared to results obtained with formamide. It is believed that the high salt content of the denaturant is incompatible with electrophoresis.

In the fifth step of this invention, the isolated primer extension products are analyzed by electrophoresis. This is accomplished using techniques well known by those who practice the art.

Isolation of primer extension products by capture and release from a solid-supported reagent is not limited to using the biotin-avidin binding pair. Other binding pairs are known (and will continue to be discovered) which could be applied to this invention. Many of these binding pairs are of the antibody-antigen type. The antigenic group could be attached to the primer at a site which doesn't interfere with primer extension or binding to the antibody. Anti-digoxigenin antibodies, for example, bind tightly to nucleic acids tagged with digoxigenin and such digoxigenin-based reporter systems work as well as those based on the biotin-avidin binding pair. Primer extension products could be captured and released by antibodies bound to or covalently linked to a solid support. Techniques for attaching antibodies to solid supports and linking of antigenic groups to other molecules are known.

EXAMPLES

The following examples illustrate, but do not limit, the process of the present invention. To demonstrate the specificity of this process for the selective binding of only biotinylated fragments, and therefore its ability to separate primer extension products from other DNA which might be present in reaction mixtures, Examples 1 to 4 illustrate DNA sequencing reactions using both biotinylated and nonbiotinylated primers. The non-biotinylated primers were added to simulate the presence of nucleic acid impurities which can interfere with DNA sequencing. These examples clearly demonstrate that the processes of the present invention are capable of isolating biotinylated primer extension products while removing artifacts derived from non-biotinylated nucleic acids. Example 1 discloses the use of a 5'-end biotinylated oligonucleotide in sequencing DNA, specific interaction of the biotinylated fragments with streptavidin coated $CrO_2$ particles, and subsequent release of the biotin-streptavidin complexes for analysis on sequencing gels. Example 2 demonstrates the same reaction as Example 1 but the DNA was heated prior to addition of the streptavidin particles. In Example 3, the reaction was the same as Example 1 except that the DNA was digested with a single stranded DNA nuclease prior to addition of the particles. Example 4 demonstrates the same reaction as Example 1 but the DNA was treated with a strong base prior to addition of the particles. Example 5 demonstrates the improved gel resolution of the DNA sequencing fragments and higher signal when captured and analyzed on a fluorescent DNA detection system. Example 6 demonstrates that a biotinylated primer can be captured on strept/avidin-coated particles, enzymatically extended, dissociated, and analyzed. Example 7 demonstrates, by recapture, that the biotin subunit of complexed biotinylated nucleic acids is not destroyed by dissociating the biotin-strept/avidin complex.

Example 1

Specific Capture of Biotinylated DNA Strands Using Streptavidin Particles

The following process, formatted into three reaction steps, consists of sequencing of single stranded DNA with both biotinylated and nonbiotinylated oligonucleotides, capturing only the biotinylated DNA fragments, and then analyzing these fragments on a DNA sequencing gel.

Step 1

To a 1.5 mL microcentrifuge tube (labelled "A") were added 4 uL (1.3 ug) of M13mp18 DNA (New England Nuclear, Boston, Mass.), 1 uL (5 ng) of primer A (5'-GTTTTCCCAGTCACGAC-3'), 2 uL of 5× annealing buffer consisting of 200 mM Tris-HCl, pH 7.5; 100 mM $MgCl_2$; 250 mM NaCl (United States Biochemical Corporation, Cleveland, Ohio). To a separate 1.5 mL microcentrifuge tube (labelled "B") were added 4 uL (1.3 ug ) of M13mp18 DNA, 1 uL (5 ng) of primer B [(5'-BioGTTTTCCCAGTCAC-GAC- 3'), prepared as described in Cocuzza, Tetrahedron Letters, 30, 6287–6290 (1989), and 2 uL of 5× annealing buffer. Both tubes were then heated in a boiling water bath for 2 min, transferred to a 37° C. water bath for 10 min. and then centrifuged in a microfuge for 2 sec. To each tube were added 1 uL of 100 mM dithiothreitol (United States Biochemical Corporation, Cleveland, Ohio), 2 uL labeling mix consisting of 1.5 uM dGTP, 1.5 uM dCTP, and 1.5 uM dTTP (United States Biochemical Corporation, Cleveland, Ohio), 2 uL (20 uCi) of alpha-$^{32}$-P-dATP (3000 Ci/mmol) New England Nuclear, Boston, Mass.) and 2 uL (6 units) of Sequenase® (New England Nuclear, Boston, Mass.). The extension reaction was allowed to proceed at room temperature for 5 min. To tube "A", 12 uL of ddC mix consisting of 80 uM dGTP, 80 uM dATP, 80 uM dCTP, 80 uM dTTP, 8 uM ddCTP, and 50 mM NaCl (United States Biochemical Corporation, Cleveland, Ohio) were added. To tube "B", 12 uL of ddG mix consisting of 80 uM dGTP, 80 uM dATP, 80 uM dCTP, 80 uM dTTP, 8 uM ddGTP, and 50 mM NaCl (United States Biochemical Corporation, Cleveland, Ohio) were added. The reaction in each tube was conducted at 37° C. for 10 min. Six microliters from each tube were added to separate 1.5 mL microcentrifuge tubes, "Control A" and "Control B", each of which contained 4 uL of stop solution consisting of 95% formamide, 20 mM EDTA, 0.05% bromophenol blue, and 0.05% xylene cyanol FF (United States Biochemical Corporation, Cleveland, Ohio). These were stored at room temperature. The remaining liquid in tubes "A" and "B" were combined in a 1.5 mL microcentrifuge tube labelled "C" and 6 uL of the resulting solution was transferred to a new 1.5 mL microcentrifuge tube, labeled "Mix", which contained 4 uL of stop solution. This tube was also stored at room temperature.

Step 2

Six microliters of the combined reaction mixtures from tube "C" were added to a 1.5 mL microcentrifuge tube containing 9.6 uL of TETx composed of 10 mM Tris-HCl, pH 7.5; 1 mM EDTA; 0.17% (w/v) Triton X-100. To this were added 2.2 uL of 1.25M NaCl, 2.4 uL (3.1 ug) of bovine serum albumin (Bethesda Research Laboratories, Gaithersburg, Md.), and 10 uL (40 ug) of $CrO_2$-streptavidin particles (E. I. du Pont de Nemours & Co., Glasgow, Del.). The complexation reaction was conducted at room temperature for 30 min with gentle dispersion of the particles every 5–6 min by hand. The streptavidin-$CrO_2$ particles bearing the biotin-containing DNA fragments were coagulated on the side of the tube by placing the tube in a magnetic rack (MAGIC® Magnetic Separation Unit, Corning Glass Works Magnetic Immunochemistries). The liquid was carefully removed by pipette so as not to disturb the particles. The tube was then removed from the magnetic rack and the particles washed by suspending in 50–100 uL of TENTx buffer composed of 10 mM Tris-HCl, pH 7.5; 1 mM EDTA; 100 mM NaCl; 0.17% (w/v) Triton X-100. The tube was placed again in the magnetic rack and the liquid removed. The process of washing of the particles was repeated a total of three times. Ten microliters of stop solution were added to the particles and the resultant suspension was stored at room temperature.

Step 3

All of the DNA samples stored in stop solution were heated in a boiling water bath for 3 min and loaded onto a 6% polyacrylamide (19:1, acrylamide:bis-acrylamide), 8M urea (Bio-Rad, Richmond, Calif.) sequencing gel in TBE buffer (89 mM Tris-borate; 89 mM boric acid; 2 mM EDTA). Samples were electrophoresed in TBE buffer at 40 watts until the bromophenol dye was within 2 cm of the gel's bottom edge. The gel was transferred to a sheet of sequencing gel filter paper (Bio-Rad, Richmond, Calif.) and dried under vacuum at 80° C. for 45 min. A sheet of X-OMAT RP X-ray film (Eastman Kodak Company, Rochester, N.Y.) was placed against the gel for autoradiographic exposure. The film was developed after overnight exposure at room temperature.

Figure 3:
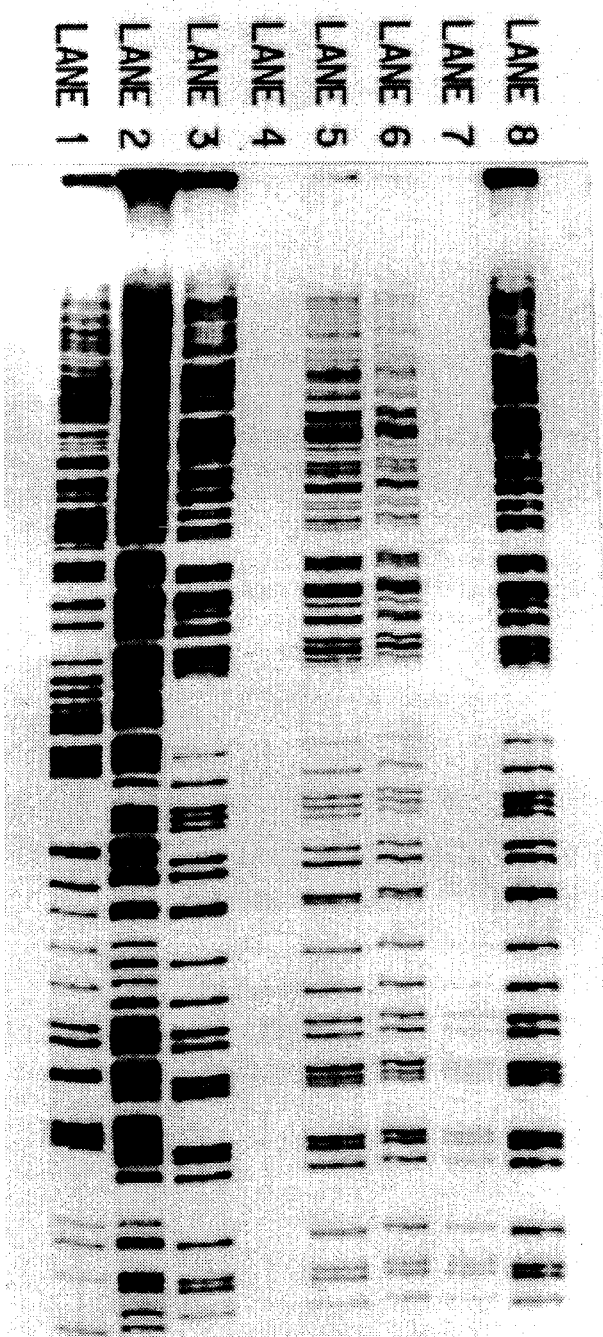
FIG. 3 is an autoradiographic film exposure of a sequencing gel showing the separation of primer extension products using solid supported ferromagnetic streptavidin.

The conclusions of this experiment are based upon the autoradiographic evidence shown in FIG. 3. Lanes 1 and 3 contain the DNA sequence fragments synthesized using a nonbiotinylated primer/ddC terminator and a biotinylated primer/ddG terminator, respectively, from the two "Control" tubes. The DNA sequence patterns of lanes 1 and 3 are clearly different. Not obvious is a slight retardation of mobility (approximately 2 bases) of the biotinylated DNA sequence fragments in lane 3 due to presence of the biotin group on the DNA fragments. Lane 2 is an equal mixture of the samples electrophoresed in lanes 1 and 3 from the tube labeled "Mix".

It is most important to compare lane 2 with lane 4. The DNA sample in lane 4 is identical to that in lane 2 except that it was treated with the streptavidin particles as described in Step 2. The bands in lane 4 demonstrate that the biotinylated DNA sequencing fragments were captured specifically in the presence of unbiotinylated fragments.

Example 2

Heat Treatment of DNA Prior to Addition of Streptavidin Particles from Example 1

Steps 1 and 3 are as described in Example 1.
Step 2 was modified as follows:

Step 2

Six microliters of the combined reactions from tube "C" were added to a 1.5 mL microcentrifuge tube containing 9.6 uL of TETx. This tube was placed in a boiling water bath for 3 min, transferred to a container of ice-water for 1 min, and then centrifuged in a microfuge for 2 sec. To this were added 2.2 uL of 1.25 M NaCl, 2.4 uL (3.1 ug) of bovine serum albumin and 10 uL (40 ug) of CrO2-streptavidin particles. The complexation reaction was conducted at room temperature for 30 min with gentle dispersion of the particles every 5–6 min by hand. The tube was then placed on a magnetic rack to coagulate the particles on one side of the tube. The liquid was carefully removed by pipette so as not to disturb the particles. The tube was then removed from the magnetic rack and 50–100 uL of TENTx buffer added to wash the particles. The tube was replaced in the magnetic rack and the supernatant again removed. The process of washing the particles was repeated a total of three times. Ten microliters of stop solution were added to the particles and the resulting suspension was stored at room temperature.

The conclusions of this experiment are based upon the autoradiographic evidence in FIG. 3. As previously described in Example 1, a comparison of lanes 2 and 4 demonstrates that the $CrO_2$-streptavidin particles specifically capture only the biotinylated DNA sequencing fragments from a DNA sequencing reaction mixture containing both biotinylated and nonbiotinylated extended primers. The DNA sample in lane 5 is identical to the DNA sample in lane 4 except that the DNA was heat denatured at 100° prior to addition of the streptavidin particles. A comparison of lane 5 to lane 2 reveals specific capture of the biotinylated fragments and a reduction of radio-labelled DNA remaining at the top of the gel.

It is most important to compare the intensity of the autoradiographic bands in lanes 4 and 5. The incorporation of a heat denaturing step in the reaction allows for improved specific capture of the biotinylated DNA strands with the streptavidin particles.

Example 3

Nuclease Treatment of DNA Prior to Addition of Streptavidin Particles from Example 1

Steps 1 and 3 are as described in Example 1.
Step 2 was modified as follows:

Step 2

Six microliters of the combined reactions from tube "C" were added to a 1.5 mL microcentrifuge tube containing 5 uL water and 3 uL 5× MB buffer composed of 25% glycerol; 10 mM $ZnSO_4$; 300 mM NaOAc, pH 5.4. To this, 1 uL (7 units) of Mung Bean nuclease (Promega Corporation, Madison, Wis.) was added and the digestion reaction was conducted at 37° C. for 5 min. Two microliters of MB Stop buffer composed of 83 mM EDTA; 1.7M Tris-HCl, pH 9.0, 2.2 uL of 1.25M NaCl, 2.4 uL (3.1 ug) of bovine serum albumin and 10 uL (40 ug) of $CrO_2$-streptavidin particles were added to the tube. The reaction was conducted at room temperature for 30 min with gentle dispersion of the particles every 5–6 min by hand. The tube was then placed on a magnetic rack to coagulate the particles on one side of the tube. The liquid was carefully removed by pipette so as not to disturb the particles. The tube was then removed from the magnetic rack and 50–100 uL of TENTx buffer were added to wash the particles. The tube was replaced in the magnetic rack and the supernatant again decanted. The process of washing the particles was repeated a total of three times. Ten microliters of stop solution were added to the particles and the resulting suspension was stored at room temperature.

The conclusions of this experiment are based upon the autoradiographic evidence in FIG. 3. As previously described in Example 1, a comparison of lanes 2 and 4 demonstrates that the $CrO_2$-streptavidin particles specifically capture only the biotinylated DNA sequencing fragments from a DNA sequencing reaction mixture containing both biotinylated and nonbiotinylated extended primers. The DNA sample in lane 6 is identical to the DNA sample in lane 4 with the exception that the DNA was treated with a single stranded DNA nuclease treatment prior to addition of the streptavidin particles. A comparison of lane 6 with lane 2 shows the specific capture of only the biotinylated fragments and a reduction of radiolabelled DNA remaining at the top of the gel.

It is most important to compare the intensity of the autoradiographic bands in lanes 4 and 6. The incorporation of a nuclease step in the reaction allows for improved specific capture of the biotinylated DNA strands by the streptavidin particles.

Base Treatment of DNA Prior to Addition of Streptavidin Particles from Example 1

Steps 1 and 3 are as described in Example 1.
Step 2 has been modified as follows:
Step 2

Six microliters of the combined reactions from tube "C" were added to a 1.5 mL microcentrifuge tube containing 2 uL 0.2 N NaOH and incubated at 37° C. for 5 min. To this were added 2 uL of 170 mM Tris-HCl, pH 3.75, 5.6 uL of TETx, 2.2 uL of 1.25M NaCl, 2.4 uL (3.1 ug) of bovine serum albumin and 10 ul (40 ug) of $CrO_2$-streptavidin particles. The reaction was conducted at room temperature for 30 min with gentle dispersion of the particles every 5–6 min by hand. The tube was then placed on a magnetic rack to coagulate the particles on one side of the tube. The liquid was carefully removed by pipette so as not to disturb the particles. The tube was then removed from the magnetic rack and 50–100 uL of TENTx buffer added to wash the particles. The tube was replaced in the magnetic rack and the supernatant again removed. The process of washing the particles was repeated a total of three times. Ten microliters of stop solution were added to the particles and the resulting suspension was stored at room temperature.

The conclusions of this experiment are based upon the autoradiographic evidence provided in FIG. 3. It is most important to compare lanes 2 and 7. The DNA sample in lane 7 is identical to the DNA sample in lane 2 with the exception that the DNA was treated with strong base followed by capture with the streptavidin particles. Lane 7 demonstrates that under these conditions specific capture of the biotinylated DNA sequencing fragments occurs.

Specific Capture of Fluorescent Biotinylated DNA Fragments and Improved Gel Resolution The following process, formatted into three reaction steps, consists of sequencing single stranded DNA with both biotinylated and nonbiotinylated oligonucleotides, capturing only the biotinylated DNA fragments and then analyzing these fragments on a DNA sequencing gel with a fluorescence detection system.

Step 1

In a 1.5 mL microcentrifuge tube were added 108 uL (27 ug) of M13mp18 DNA (New England Nuclear, Boston, Mass.), 27 uL (135 ng) of primer [(5'-BioGTTTTCCCAGT-CACGAC-3'), prepared as described in Cocuzza, Tetrahedron Letters, 30, 6287–6290 (1989), and 63 uL of 5× annealing buffer. The tube was heated in a boiling water bath for 2 min and then transferred to a 37° C. water bath for 10 min. To the tube were added 22.5 uL of 100 mM dithiothreitol, 27 uL dNTP's consisting of 75 uM deaza-dATP, 75 uM dCTP, 75 uM deaza-dGTP, and 75 uM dTTP (New England Nuclear, Boston, Mass.), 9 uL of 8 uM ddCTP(SF519) (New England Nuclear, Boston, Mass.) and 9 uL (27 units) of Sequenase® (New England Nuclear, Boston, Mass.). The extension reaction was conducted at 37° C. for 5 min. Thirty microliters were removed and centrifuged through a G-50 spin column (New England Nuclear, Boston, Mass.) which had been prewashed with water. The effluent was collected in a 1.5 mL microcentrifuge tube. The solvent was evaporated under vacuum for 30 min in a Speed-Vac concentrator (Savant Instruments, Inc., Hicksville, N.Y.), and the DNA sample was resuspended in 3 uL of G505 loading solution (New England Nuclear, Boston, Mass.) and stored at 4° C.

Step 2

To a 1.5 mL microcentrifuge tube were added 30 uL of the reaction mixture from Step 1 above and 48 uL TETx. The tube was placed in a boiling water bath for 3 min and then transfered to a container of ice-water for 2 min. To this were added 11 uL of 1.25M NaCl, 12 uL (15 ug) of bovine serum albumin (Bethesda Research Laboratories, Gaithersburg, Md.) and 50 uL (200 ug) of $CrO_2$-streptavidin particles (E. I. dupont, Glasgow, Del.). The complexation reaction was conducted at 37° C. for 30 min with gentle dispersion of the particles every 5–6 min by hand. The streptavidin-$CrO_2$ particles bearing the biotin-containing DNA fragments were coagulated on the side of the tube by placing the tube in a magnetic rack (MAGIC® Magnetic Separation Unit, Corning Glass Works Magnetic Immunochemistries). The liquid was carefully removed by pipette so as not to disturb the particles. The tube was then removed from the magnetic rack and the particles washed by suspending in 100 uL of TENTx buffer. The tube was replaced in the magnetic rack and the liquid again removed. This process of washing of the particles was repeated a total of three times. The DNA sample was resuspended in 3 uL of G505 loading solution (New England Nuclear, Boston, Mass.) and stored at 4° C.

Step 3

Both of the DNA samples were heated in a boiling water bath for 3 min and loaded onto a 6% polyacrylamide (19:1, acrylamide:bis-acrylamide), 8M urea (Bio-Rad, Richmond, Calif.) sequencing gel in TBE buffer composed of 89 mM Tris-borate; 89 mM boric acid; 2 mM EDTA. The samples were electrophoresed in TBE buffer at 22 watts in a GENESIS™ 2000 instrument (E. I. du Pont de Nemours and Company, Wilmington, Del.).

Figure 4A:
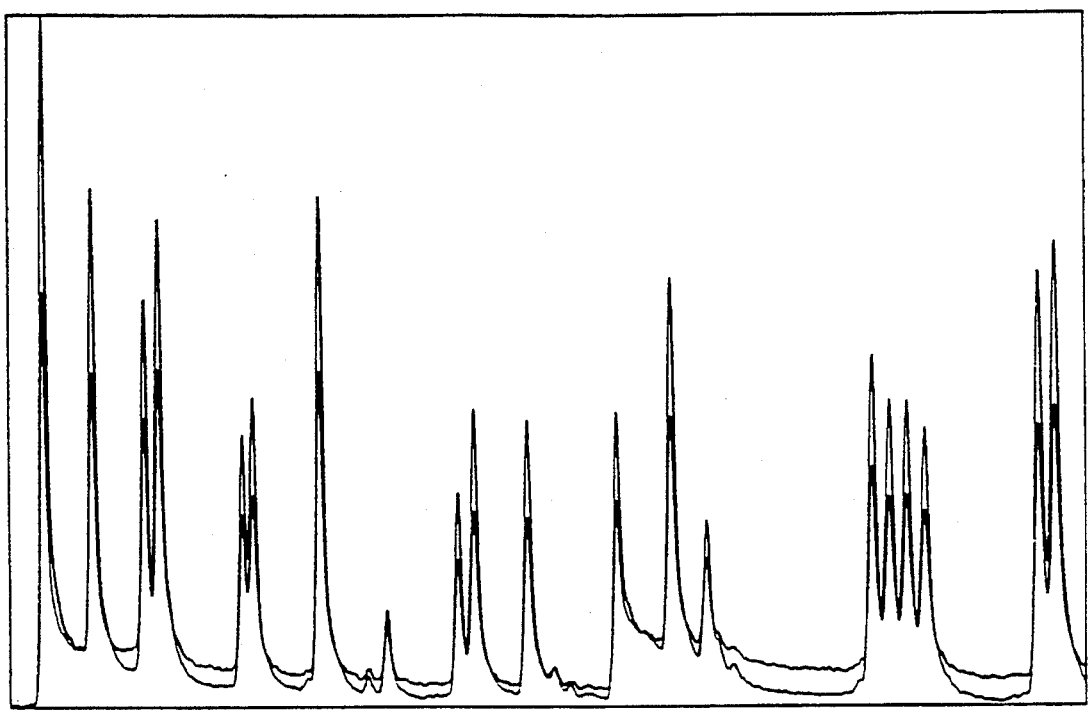
FIG. 4a is a plot from a fluorescent detector monitoring the output of a standard DNA sequencing run where solid supported ferromagnetic streptavidin is not employed.
Figure 4B:
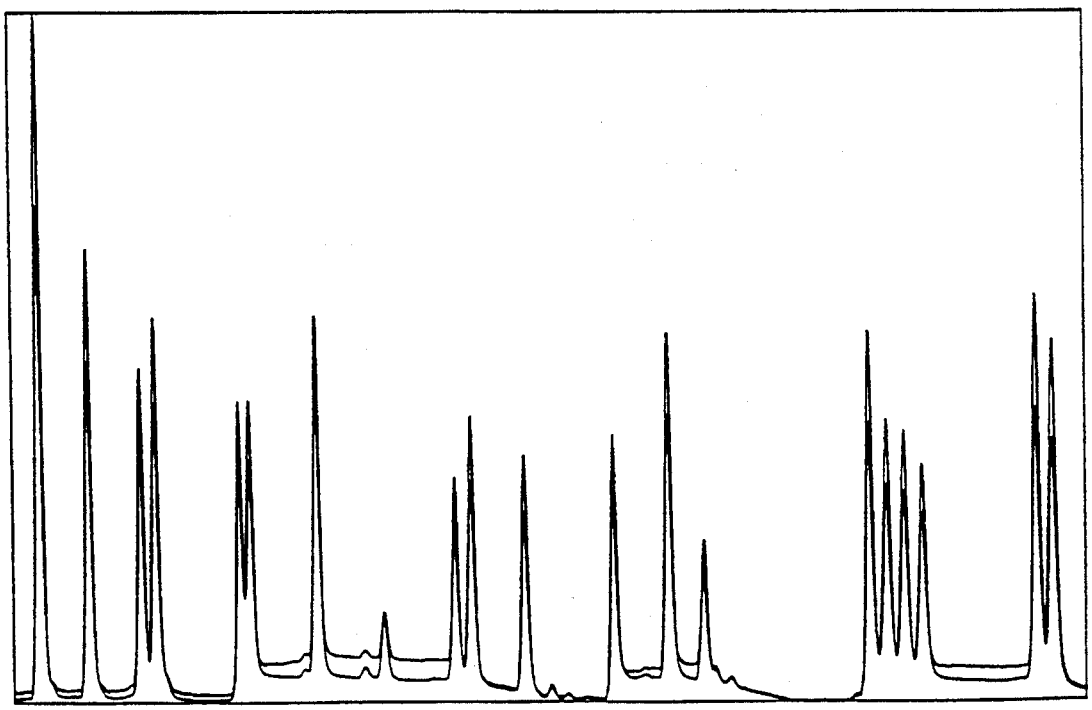
FIG. 4b is a plot from a fluorescent detector monitoring the output of a DNA sequencing run where solid supported ferromagnetic streptavidin is employed.

The conclusions of this experiment are based upon the graphic output from the GENESIS™ 2000 shown in FIGS. 4a and b. FIG. 4a shows the data from a standard noncaptured DNA sequencing run. FIG. 4b shows the data from the biotin-streptavidin capture method of Step 2 above. A comparison of the fluorescent signal of FIG. 4a and FIG. 4b shows that FIG. 4b has a higher signal.

Figure 5:
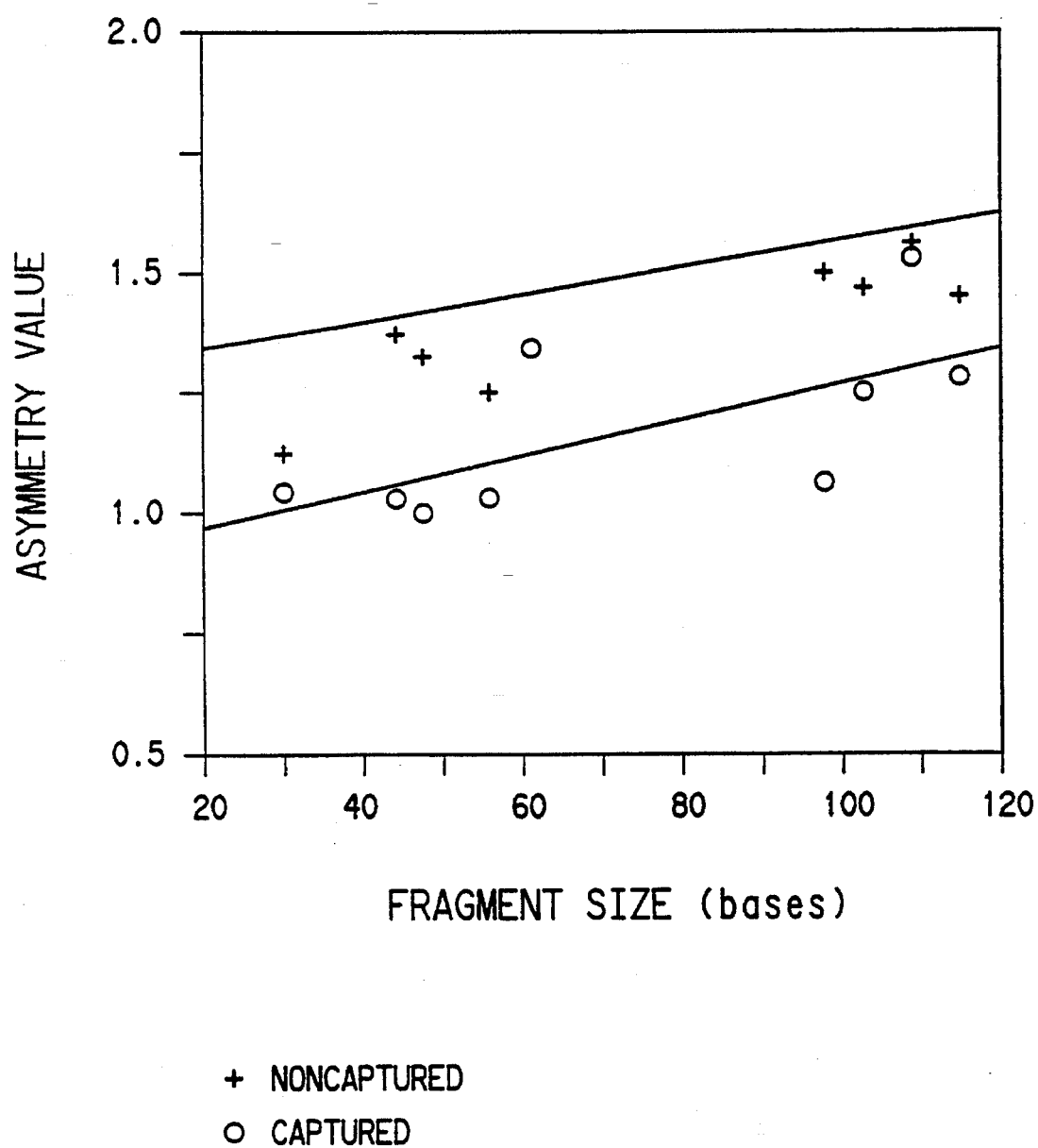
FIG. 5 represents a plot of peak asymmetry values taken from the data shown in FIG. 4a and 4b as a function of DNA fragment size.

It is most important to compare the resolution of the peaks in FIGS. 4a and 4b. Since peak asymmetry is inversely related to resolution, FIG. 5 presents a plot of asymmetry values as a function of fragment size. It can be seen that captured DNA samples give improved peak shapes (and consequently better resolution) over the standard noncaptured DNA.

EXAMPLE 6

Sequencing with a Biotinylated Primer Bound to Streptavidin Coated Particles

Step 3 is as described in Example 1.
Steps 1 and 2 were modified as follows:

Step 1

In a 1.5 mL microcentrifuge tube were added 1 uL (5 ng) of primer [(5'-BioGTTTTCCCAGTCACGAC-3'), prepared as described in Cocuzza, Tetrahedron Letters, 30, 6287–6290 (1989), and 10 uL (40 ug) of $CrO_2$-streptavidin particles (E. I. du Pont de Nemours & Co., Wilmington, Del.). The complexation reaction was conducted at room temperature for 20 min with gentle dispersion of the particles every 5–6 min by hand. The streptavidin-$CrO_2$ particles bearing the biotinylated primer were immobilized on the side of the tube by placing the tube in a magnetic rack (MAGIC® Magnetic Separation Unit, Corning Glass Works Magnetic Immunochemistries, Corning, N.Y.). The liquid was carefully removed so as not to disturb the particles. The tube was then removed from the magnetic rack and the particles washed by suspending in 50 uL of TENTx buffer. The tube was placed again in the magnetic rack and the liquid removed. The process of washing of the particles was repeated a total of three times using TENTx buffer and a final wash using TE buffer composed of 10 mM Tris-HCl, pH 7.5, 1 mM EDTA.

Step 2

To the captured primer from Step 1 were added 4 uL (1 ug) of M13mp18 DNA (New England Nuclear, Boston, Mass.), 2 uL of 5× annealing buffer and 3 uL of water. The tube was heated in a 37° C. water bath for 4 min. To the tube were added 1 uL of 100 mM dithiothreitol (United States Biochemical Corporation, Cleveland, Ohio), 2 uL labeling mix composed of 1.5 uM dGTP, 1.5 uM dCTP, 1.5 uMdTTP (United States Biochemical Corporation, Cleveland, Ohio), 2 uL (20 Uci) of alpha-$^{32}$P-dATP (3000 Ci/mmol; New England Nuclear, Boston, Mass.) and 2 uL (6 units) of Sequenase® (New England Nuclear, Boston, Mass.). The reaction was allowed to proceed at room temperature for 5 min. To the tube were added 12 uL of ddT mix composed of 80 uM dGTP, 80 uM dATP, 80 uM dCTP, 80 uM dTTP, 8 uM ddTTP, 50 mM NaCl (United States Biochemical Corporation, Cleveland, Ohio) and the reaction conducted at 37° C. for 10 min. The streptavidin-$CrO_2$ particles bearing biotin-containing DNA fragments were immmobilized on the side of the tube by placing the tube in a magnetic rack (MAGIC® Magnetic Separation Unit, Corning Glass Works Magnetic Immunochemistries). The liquid was carefully removed so as not to disturb the particles. The tube was then removed from the magnetic rack and the particles washed by suspending in 50 uL of TENTx buffer. The tube was placed again in the magnetic rack and the liquid removed. The process of washing of the particles was repeated a total of three times. Ten microliters of stop solution were added to the particles and the resultant suspension was stored at room temperature.

Figure 6:
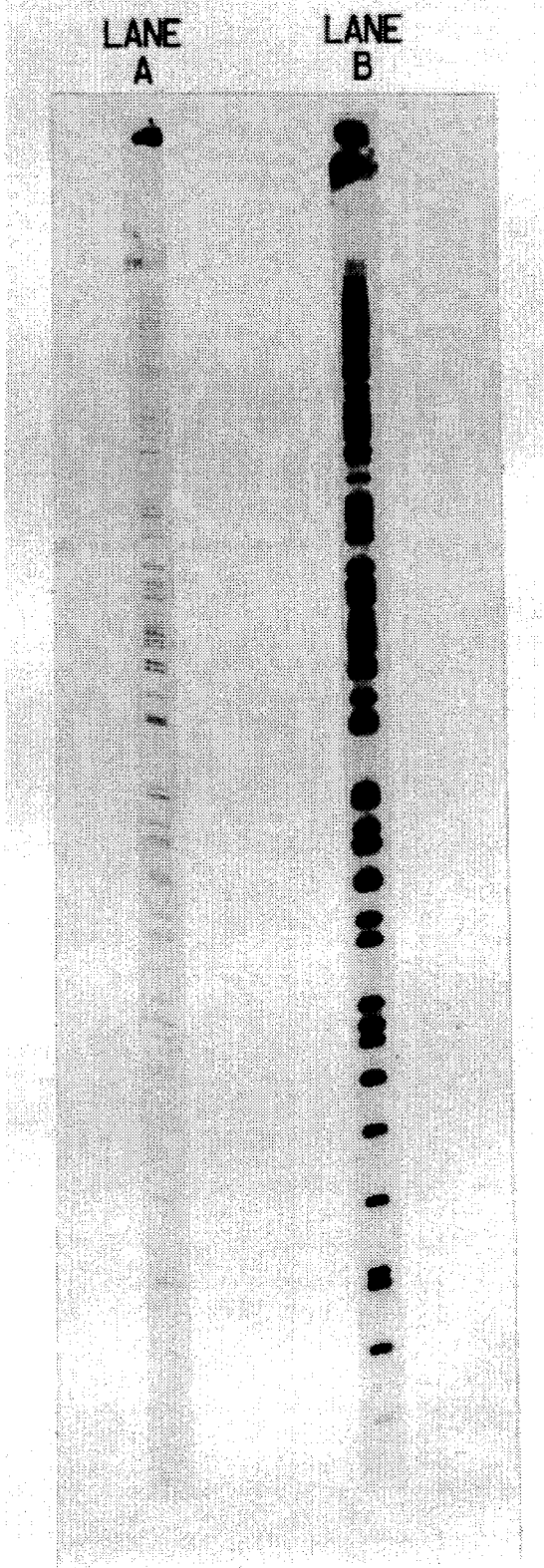
FIG. 6 is an autoradiographic film exposure of a sequencing gel comparing DNA sequence patterns where the biotinylated primer was complexed to the streptavidin particles prior to sequencing reactions rs. patterns of DNA where the biotinylated primer was first extended in sequencing reactions and then complexed to the streptavidin particles.

The conclusions of this experiment are based upon the autoradiographic evidence provided in FIG. 6. Under these conditions, sequence information was obtained using a biotinylated primer already complexed to the particles. Lane A shows sequence information obtained using a biotinylated primer already complexed to the particles prior to the sequencing reaction. This demonstrates the ability to first complex the biotinylated oligonucleotide to the streptavidin particles and then perform the sequencing reaction without any subsequent capturing. Lane B, shown as a control, is similar to lane 5 of FIG. 3 in that the sequencing reaction was heat denatured at 95° C. and then the biotinylated DNA was complexed to the streptavidin coated particles. This process eliminates the need to capture after the sequencing reaction as in Examples 1–5.

EXAMPLE 7

Recapture of Biotinylated DNA Fragments

Step 1

In a 1.5 mL microcentrifuge tube were added 84 uL (21 ug) of M13mp18 DNA (New England Nucelar, Boston, Mass.), 21 uL (105 ng) of primer [(5'-BioGTTTTCCCAGT-CACGAC- 3'), prepared as described in Cocuzza, Tetrahedron Letters, 30, 6287–6290 (1989), and 49 uL of 5× annealing buffer. The tube was heated in a boiling water bath for 2 min and then transferred to a 37° C. water bath for 10 min. To the tube were added 17.5 uL of 100 mM dithiothreitol, 21 uL dNTP's (75 uM deaza-dATP, 75 uM dCTP, 75 uM deaza-dGTP, 75 uM dTTP, New England Nuclear, Boston, Mass.), 7 uL of 8 uM ddCTP (SF519) (New England Nuclear, Boston, Mass.) and 7 uL (21 units) of Sequenase® (New England Nuclear, Boston, Mass.). The reaction was conducted at 37° C. for 5 min.

Step 2

In two separate 1.5 mL microcentrifuge tubes were added 30 uL of the reaction from Step 1 above and 88 uL TETx (10 mM Tris-HCl, pH 7.5, 1 mM EDTA, 0.17% (w/v) Triton X-100). The tubes were placed in a boiling water bath for 3 min and then transferred to a container of ice-water for 2 min. To this were added 11 uL of 1.25M NaCl, 12 uL (15 ug) of bovine serum albumin (Bethesda Research Laboratories, Gaithersburg, Md.) and 10 uL (300 ug) of DYNABEADS™ M-280 (DYNAL, Inc., Great Neck, N.Y.). The reaction was conducted at 37° C. for 30 min with gentle dispersion of the particles every 5–6 min by hand. The streptavidin coated particles bearing the biotin-containing DNA fragments were immobilized on the side of the tubes by placing the tubes in a magnetic rack (MAGIC® Magnetic Separation Unit, Corning Glass Works Magnetic Immunochemistries ). The liquid was carefully removed so as not to disturb the particles. The tubes were then removed from the magnetic rack and the particles washed by suspending in 150 uL of TENTx buffer. The tubes were placed again in the magnetic rack and the liquid removed. The process of washing of the particles was repeated a total of three times. The DNA sample in one of the tubes was then resuspended in 3 uL of formamide and labelled "recapture". The DNA sample in the other tube was then resuspended in 3 uL of G505 loading solution (New England Nuclear, Boston, Mass.).

Step 3

The tube labelled "recapture" was heated in a boiling water bath for 3 min and then transferred to as container of ice-water for 2 min. To this were added 15 uL TETx, 11 uL of 1.25M NaCl, 12 uL (15 ug) of bovine serum albumin (Bethesda Research Laboratories, Gaithersburg, Md.) and 10 uL (300 ug) of DYNABEADS™ M-280 (DYNAL, Inc., Great Neck, N.Y.). The reaction was conducted at 37° C. for 30 min with gentle dispersion of the particles every 5–6 min by hand. The streptavidin coated particles bearing the biotin-containing DNA fragments were immobilized on the side of the tube by placing the tube in a magnetic rack (MAGIC® Magnetic Separation Unit, Corning Glass Works Magnetic Immunochemistries). The liquid was carefully removed so as not to disturb the particles. The tube was then removed from the magnetic rack and the particles washed by suspending in 150 uL of TENTx buffer. The tube was placed again in the magnetic rack and the liquid removed. The process of washing of the particles was repeated a total of three times. The DNA sample was resuspended in 3 uL of G505 loading solution (New England Nuclear, Boston, Mass.).

Step 4

The DNA samples were heated in a boiling water bath for 3 min and loaded onto a 6% polyacrylamide (19:1, acrylamide:bis-acrylamide), 8M urea (Bio-Rad, Richmond, Calif.) sequencing gel in TBE buffer (89 mM Trisborate, 89 mM boric acid, 2 mM EDTA). The sample .was electrophoresed in TBE buffer at 22 watts in a GENESIS™ 2000 instrument.

Figure 7A:
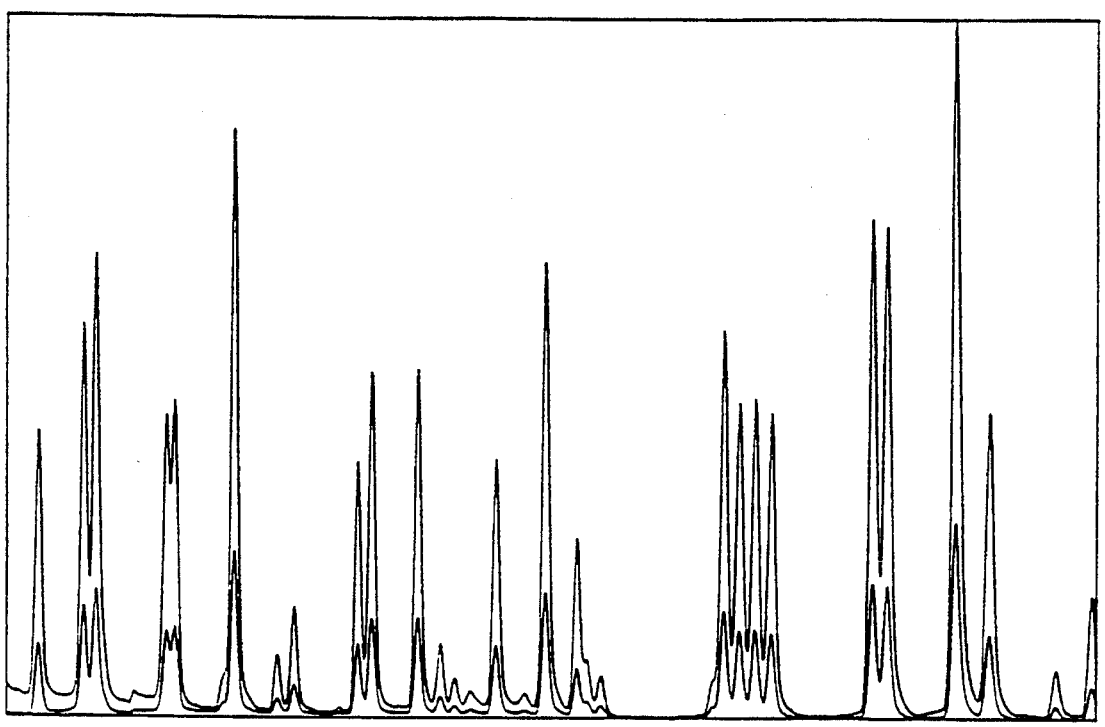
FIG. 7a is a plot from a fluorescent detector monitoring the output of a standard biotin-streptavidin captured DNA sequencing run.
Figure 7B:
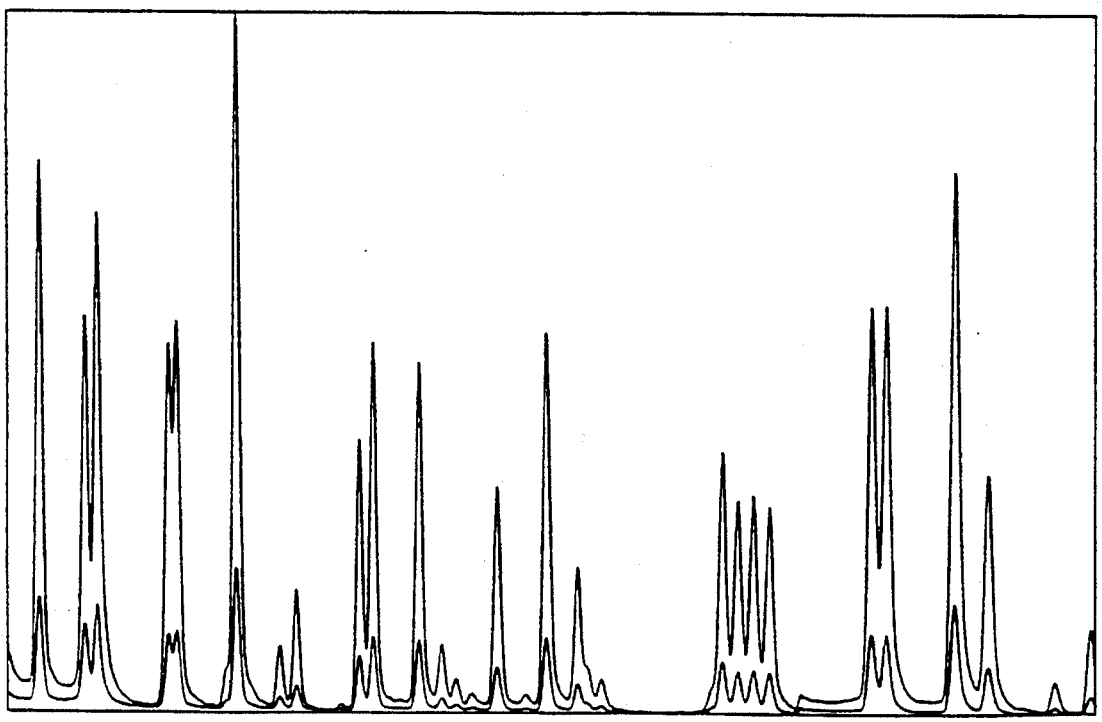
FIG. 7b is a plot from a fluorescent detector monitoring the output of a recaptured biotin-streptavidin DNA sequencing run.

The conclusions of this experiment are based upon the graphic output from the GENESIS™ 2000 shown in FIGS. 7a and 7b. FIG. 7a shows the data from a standard biotin-streptavidin captured DNA sequencing run. FIG. 7b shows the data from the biotin-streptavidin recaptured DNA sequencing run. It can be seen that the captured and subsequent released biotinylated DNA fragments can be recaptured with added streptavidin coated particles. These data demonstrate that the dissociated biotinylated fragments have an uncomplexed biotin group which can be recaptured by streptavidin particles.

It will be apparent that the instant specification and examples are set forth by way of illustration and not limitation, and that various modifications and changes may be made without departing from the spirit and scope of the present invention.

We claim:

1. In an improved method for sequencing DNA wherein the following steps are conventional:
   (a) extending a primer by means of a template-directed primer extension reaction; and
   (b) analyzing the primer extension products by means of gel electrophoresis, the improvement comprising:
      (i) extending a biotinylated primer by means of a template-directed primer extension reaction to produce biotinylated primer extension products;
      (ii) complexing the biotin of said biotinylated primer extension products of step (i) with a biotin-binding protein immobilized on a solid support, said complexing performed either before or after separating the template from the biotinylated primer extension products of step (i);
      (iii) separating physically the complexed biotinylated primer extension products of step (ii) from the liquid phase of the primer extension reaction;
      (iv) treating the complex of step (iii) with formamide compatible with gel-electrophoresis to dissociate the biotin of said biotinylated primer extension products from the immobilized biotin-binding protein;
      (v) analyzing the biotinylated primer extension products of step (iv) by means of gel electrophoresis; and
      (vi) sequencing the DNA of the primer extension products obtained.

2. The method of claim 1 wherein the biotinylated primer is extended in step (i) by means of a template, a polymerase, and one or more nucleoside triphosphates.

3. The method of claim 1 wherein the biotin in the biotinylated primer is linked through the 5'-hydroxyl group of the primer.

4. The method of claim 1 wherein the biotinylated primer extension products of step (i) are treated with a strong base, heat, a single-strand nuclease, or formamide.

5. The method of claim 4 wherein the products of step (i) are treated with a strong base.

6. The method of claim 4 wherein the products of step (i) are treated with heat at a temperature between 25° and 100° C.

7. The method of claim 4 wherein the products of step (i) are treated with a single-strand nuclease.

8. The method of claim 1 wherein, in step (ii), the solid support is selected from the group consisting of polymeric beads, and magnetic particles, and paper, plastic and glass surfaces.

9. The method of claim 8 wherein the magnetic particles are chromium dioxide particles.

10. The method of claim 2, wherein, in step (ii), the biotin-binding protein is selected from the group consisting of avidin, streptavidin, and anti-biotin antibodies.

11. The method of claim 1 wherein said electrophoresis-compatible formamide is heated to a temperature about 25° C. to 100° C.

12. A method for ioslating primer extension products from template-directed extension reactions comprising the following steps:
   (a) complexing the biotin of a biotinylated primer to a biotin-binding protein immobilized on a solid support;
   (b) extending the complexed biotinylated primer of step (a) by means of a template-directed primer extension reaction;
   (c) separating the template from the complexed biotinylated primer extension products of step (b);
   (d) separating physically the complexed biotinylated primer extension products of step (c) from the liquid phase of the primer extension reaction;
   (e) treating the complex of step (d) with formamide to dissociate the biotin of said biotinylated primer extension products from the biotin-binding protein immobilized on a solid support; and
   (f) sequencing the DNA of the primer extension products obtained.

13. The method of claim 12 wherein the biotin is linked through the 5'-hydroxyl group of the primer.

14. The method of claim 12 wherein, in step a, the solid support is selected from the group consisting of polymeric beads, magnetic particles, and paper, plastic and glass surfaces.

15. The method of claim 14 wherein the magnetic particles are chromium dioxide particles.

16. The method of claim 12 wherein, in step a, the biotin-binding protein is selected from the group consisting of avidin, streptavidin, and anti-biotin antibodies.

17. The method of claim 12 wherein the biotinylated primer is extended in step b by means of a template, a polymerase, and one or more nucleoside triphosphates.

18. The method of claim 12 wherein step c is accomplished by treating the products of step b with a strong base, heat, or a single-strand nuclease.

19. The method of claim 12 wherein the products of step b are treated with a strong base.

20. The method of claim 12 wherein the products of step b are treated with heat at a temperature of about 25° C. to 100° C.

21. The method of claim 12 wherein the products of step b are treated with a single-strand nuclease.

22. The method of claim 12 wherein the electrophoresis-compatible formamide is heated to a temperature about 25° C. to 100° C.

23. A method for isolating primer extension products from template-directed polymerase extension reactions comprising the following steps;
    (a) extending a 5'-biotinylated primer by means of a template-directed polymerase extension reaction;
    (b) separating the template from the 5'-biotinylated extension products of step (a) by the use of mung bean nuclease;
    (c) complexing the biotin of the 5'-biotinylated extension products of step (a) with streptavidin on streptavidin-coated chromium dioxide particles;
    (d) separating physically the complex of step (c) from the liquid phase of the primer extension reaction by means of a magnet;
    (e) treating the complex of step (d) with formamide heated to a temperature between about 25° C. to 100° C. to dissociate the biotin of the 5'-biotinylated primer extension products from the streptavidin-coated chromium dioxide particles; and
    (f) resolving the size the 5'-biotinylated primer extension products of step (e) by means of DNA sequencing of the primer extension products.

24. A method for isolating primer extension products from template-directed polymerase reactions comprising the following steps:
    (a) extending a 5'-biotinylated oligonucleotide primer by means of a template-directed polymerase extension reaction;
    (b) separating the template from the 5'-biotinylated extension products of step (a) by heating at a temperature of about 25° C. to 100° C.;
    (c) complexing the biotin of the 5'-biotinylated extension products of step (a) with streptavidin on streptavidin-coated chromium dioxide particles;
    (d) separating physically the complex of step (c) from the liquid phase of the primer extension reaction by means of a magnet;
    (e) treating the complex of step (d) with formamide heated to a temperature between about 25° C. to 100° C.;
    (f) analyzing the 5'-biotinylated primer extension products of step (d) by means of DNA sequencing; and
    (g) sequencing the DNA of the primer extension products obtained.

25. A method for dissociating a complex, said complex consisting essentially of biotinylated primer extension products and solid-supported biotin-binding protein immobilized on a solid support, comprising treating said complex with formamide.

26. The method of claim 25 wherein the formamide is heated to a temperature between about 25° C. to 100° C.

27. A method for dissociating a complex, said complex consisting essentially of a biotinylated nucleic acid and a biotin-binding protein, comprising treating said complex with formamide heated to a temperature between about 25° C. to 100° C.

28. The method of claim 6, 11, 13, 20, 22, 23,, 24, 25 or 27 wherein the formamide is heated to a temperature of about 95° C.

29. The method of claim 7 or 21 wherein the single-strand nuclease is mung bean nuclease.

* * * * *